United States Patent [19]

Comoglio et al.

[11] Patent Number: 5,571,509
[45] Date of Patent: Nov. 5, 1996

[54] TRUNCATED FORMS OF THE HEPATOCYTE GROWTH FACTOR (HGF) RECEPTOR

[75] Inventors: Paolo Comoglio; Tiziana Crepaldi; Maria Prat, all of Turin, Italy

[73] Assignee: Farmitalia Carlo Erba S.R.L., Milan, Italy

[21] Appl. No.: 879,384

[22] Filed: May 7, 1992

[30] Foreign Application Priority Data

May 10, 1991 [GB] United Kingdom .................. 9110202
Nov. 22, 1991 [GB] United Kingdom .................. 9124896

[51] Int. Cl.$^6$ ............................. C12N 9/10; C12N 9/12; A61K 38/45
[52] U.S. Cl. .................. 424/94.5; 435/193; 435/194
[58] Field of Search ................................ 435/70.3, 70.4, 435/193, 194; 424/94.1, 94.5; 536/23.2

[56] References Cited

FOREIGN PATENT DOCUMENTS

WO91/09974  7/1991  WIPO.

OTHER PUBLICATIONS

Biological Abstracts.–Microfilms. Abstr. No. 115341, vol. 86, No. 11, 1988 Philadelphia, PA US P. R. Tempest et al.: "Structure of the met protein and and variation of met protein kinase activity among human tumor cell lines".

Biological Abstracts.–Microfilms. Abstra. No. 124441, vol. 90, No. 11 Philadelphia, PA US p. 87096; A Iyer et al.: "Structure, tissue tissue–specific expression, and transforming activity of the mouse met protooncogene." (1990).

Cell. vol. 59, 1989, Cambridge, NA US, pp. 335–348; B. Mosley et al.: "The Murine Interleukin–4 Receptor: Molecular Cloning and Characterization of Secreted and Membrane Bound Form".

Prat, M. et al., *C–Terminal Truncated Forms of Met, the Hepatocyte Growth Factor Receptor*, Molecular and Cellular Biology, vol. 11, No. 12, pp. 5954–5962, Dec. 1991.

Naldini, L. et al., *The tyrosine Kinase Encoded by the MET Proto–Oncogene is Activated by Autophosphorylation*, Molecular and Cellular Biology, vol. 11, No. 4, pp. 1793–1803, Apr. 1991.

Ponzetto, C. et al., *c–met is amplifieled but not mutated in a cell line with an activated met tyrosine kinase*, Oncogene, vol. 6, pp. 553–559, 1991.

Gandino, L. et al., *Protein Kinase–c Activation Inhibits Tyrosine Phosphorylation of the c–met Protein*, Oncogene, vol. 5, pp. 721–725, 1990.

Gonzatti–Haces, M. et al. *PNAS* 85:21–25 (1988).

*Primary Examiner*—Dian C. Jacobson
*Attorney, Agent, or Firm*—Nikaido, Marmelstein, Murray & Oram LLP

[57] ABSTRACT

A protein, which is useful as an antagonist of hepatocyte growth factor, is composed of two disulphide-linked chains of 50 kDa and 75 or 85 kDa respectively, the 5 kDa chain being the α-chain of the tyrosine kinase encoded by the MET protooncogene and the 75 or 85 kDa chain being a C-terminal truncated form of the β-chain of the said tyrosine kinase.

2 Claims, 7 Drawing Sheets

TRUNCATED FORMS OF THE HEPATOCYTE GROWTH FACTOR (HGF) RECEPTOR

The present invention relates to truncated forms of the Hepatocyte Growth Factor (HGF) receptor, to their preparation and to pharmaceutical compositions containing them.

The MET protooncogene (Cooper et al, Nature 311, 29–33, 1984; Dean et al, Nature 318, 385–388, 1985; Park et al, PNAS USA 84, 6379–6383, 1987) encodes a transmembrane glycoprotein (p190$^{MET}$ or Met receptor) with unique features, being a heterodimer composed of two disulfide-linked chains of 50 Kda (p50$^\alpha$) and 145 Kda (p145$^\beta$) (Giordano et al, Mol. Cell. Biol. 8, 3510–3517, 1988; Giordano et al, Nature 339, 155–156, 1989). Both chains are exposed at the cell surface. The β chain spans the plasma membrane with a hydrophobic amino acid stretch and possesses an intracellular tyrosine kinase domain (Dean et al, 1985; Gonzatti-Haces et al, PNAS USA 85, 21–25, 1988; Tempest et al, FEBS Lett. 209, 3527–361, 1986). The receptor is synthesized as a 170 kDa precursor that is glycosylated and enzymatically cleaved to give the mature heterodimer (Giordano et al. Oncogene, 4, 1383–1388, 1989; Tempest et al., Br. J. Cancer 58, 3–7, 1988).

Recently, Hepatocyte Growth Factor (HGF) has been proposed as the ligand for the Met receptor (Bottaro et al., Science 251, 803–804, 1991; Naldini et al, Oncogene 6, 501–504, 1991; Naldini et al, 1991, EMBO J., 10, 2867–2878). HGF, also known as Hepatopoietin-A (Miyazawa et al., Biochem. Biphys. Res. Commun. 163 967–973 (1989); Nakamura et al., Nature 342, 440–443, 1989; Zarnegar et al. Cancer Res. 49, 3314, 1989) has been described as the most potent mitogen for rat and human hepatocytes in primary cultures and as a hepatotrophic factor involved in liver regeneration in vivo, both in humans and in rodents (for a review see Michalopoulos, FASEB J. 4, 176–187, 1990). In rats and rabbits HGF was also detected in the pancreas, salivary glands, duodenum, thyroid, and selected areas of the central nervous system (Tashiro et al., Proc. Natl. Acad-Sci. USA 87, 3200–3204, 1990; Zarnegar et al., Proc. Natl. Acad-Sci. USA 87, 1252–1256, 1990).

The MET oncogene was originally identified by transfection, using DNA from a human cell line treated with a chemical carcinogen (Cooper et al., Nature 311, 29–33, 1984). In this cell line the MET gene was activated by a chromosomal rearrangement (Park et al., Cell 45, 895 (1986)). MET was also found to be amplified and activated in a human gastric carcinoma cell line (Giordano et al., Mol. Cell Biol. 8, 3510, 1988) and in spontaneously transformed mouse fibroblasts (Cooper et al., EMBO J., 5, 2623, 1986).

We have now developed monoclonal antibodies specific for the extracellular domain and used them to screen several human cell lines Besides the known p190$^{MET}$, these antibodies consistently recognized two other Met heterodimers: a 140 kDa complex localized at the cell surface, and a 130 kDa complex released in the culture medium. Both complexes consist of an α chain indistinguishable from p50$^\alpha$, and of a C-terminal truncated β chain (p85$^\beta$ and p75$^\beta$, respectively), lacking the cytoplasmic kinase domain. These truncated Met forms are generated in vivo by posttranslational proteolytic processing. Protein kinase C activation up-regulates p130$^{MET}$ release in the culture medium.

Truncated forms of growth factor receptors have been described in several cells, tissue culture supernatants and biological fluids (Beguin et al., 1988, Proc. Natl. Acad. Sci. U.S.A., 85,637–640; DiStefano et al 1988, Proc. Natl. Acad. Sci. U.S.A. 85, 270–274; Johnson et al., 1990, Mol. Cell. Biol., 10, 4728–4736; Mosley et al., 1989, Cell, 59, 335–348; Zabrescky et al., 1991, J. Biol. Chem., 266, 1716–1720). Recently it has been reported that soluble forms of C-terminal truncated receptors can compete with the intact receptor for ligand binding and can interfere with ligand-induced stimulation of tyrosine kinase activity by forming inactive heterodimers (Basu et al., 1989, Mol. Cell. Biol., 9, 671–677; Kashles et al., 1991, Mol. Cell. Biol., 11, 1454–1463; Ueno et at., 1991, Science, 252, 844–848).

Accordingly, the present invention provides a protein which is composed of two disulphide-linked chains of 50 kDa and 75 or 85 kDa respectively, the 50 kDa chain being the α-chain of the tyrosine kinase encoded by the MET protooncogene and the 75 or 85 kDa chain being a C-terminal truncated form of the β-chain of the said tyrosine kinase.

The two C-terminal truncated Met proteins according to the invention are a 140 kDa trans-membrane form (p140$^{MET}$) and a 130 kDa soluble protein, which is released in the culture medium (p130$^{MET}$). These truncated forms are detectable in the GTL-16 human gastric carcinoma cell line, where the MET gene is amplified and overexpressed (Giordano et al, 1988) as well as in other carcinoma cell lines with normal levels of MET expression.

The truncated Met proteins have the same heterodimeric structure of the intact p190$^{MET}$, consisting of two disulfide-bonded chains. The α chains of the truncated forms are indistinguishable from the α chain of p190$^{MET}$, while their β chains have a lower molecular weight. The β chain of p140$^{MET}$ is about 85 kDa (p85$^\beta$), while the β chain of p130$^{MET}$ is about 75 kDa (p75$^\beta$).

Both p85$^\beta$ and p75$^\beta$ are truncated at their C-termini. They are not recognized by antibodies directed against a C-terminal nonadecapeptide predicted from the MET sequence. They lack the cytoplasmic tyrosine kinase domain containing Tyr$^{1235}$, the major in vitro phosphorylation site, as shown by the fact that they are not phosphorylated on tyrosine, in vivo or in vitro. P85$^\beta$ and p75$^\beta$ share the N-terminal domain with p145$^\beta$, since they are all recognized by monoclonal antibodies defining four different epitopes, and they have the same extracellular tryptic peptides.

The p85$^\beta$ chain is believed to be a transmembrane glycoprotein, which has lost most of its cytoplasmic domain. Based on the predicted aminoacid sequence, a cleavage of the last 435 C-terminal aminoacids would reduce the molecular mass by about 50 kDa. This value is consistent with the observed difference in electrophoretic migration of the intact versus the truncated β chains. P75$^\beta$ lacks the cytoplasmic domain and the transmembrane segment since it is released in the culture supernatant and does not associate with the cell membrane. Moreover it shows a 10 kDa reduction when compared with the membrane-spanning p85$^\beta$ chain. This reduction in size is compatible with the loss of a segment including the transmembrane domain.

The proteins of the invention may be obtained from cultures of cell lines in which the MET gene is expressed. Typically the cell lines are carcinoma cell lines. Accordingly, the present invention provides a process for the preparation of a protein of the invention in which the C-terminal truncated form of the β-chain is the 75 kDa chain, which process comprises:

(i) culturing cells, which express the MET gene, in a medium therefor;

(ii) contacting the resulting conditioned medium with an antibody specific for the extracellular domain of the β-chain of the tyrosine kinase encoded by the MET gene; and (iii) releasing the said protein from the resulting immunocomplex.

The cells which express the MET gene may be cells of any appropriate cell line. Suitable cells are cells of gastric carcinoma, lung adenocarcinoma, oral carcinoma and colon carcinoma cell lines. Preferably, cells overexpressing the MET gene are used. The culture medium may be any medium containing an assimilable source of carbon, an assimilable source of nitrogen and, as desired, mineral salts. RPMI 1640 medium, optionally supplemented with foetal calf serum, is a useful medium.

An antibody specific for the extracellular domain of the β-chain of the tyrosine kinase encoded by the MET gene may be raised in conventional fashion. The antibody is typically a monoclonal antibody (Kohler and Milstein, Nature 256, 495–497, 1975). Hybridoma cells producing monoclonal antibody may be prepared by fusing spleen cells from an immunised animal with a tumour cell. The mammal which is immunised may be a rat or mouse. The mammal may be immunised with whole cells, or extracts of cells, which express the MET gene. Preferably the cells overexpress the MET gene. Antibodies produced by the hybridomas are screened by assessing their ability to immunoprecipitate Met protein extracted from a Met protein-producing cell line. The hybridomas may be grown in culture or injected intraperitoneally for formation of ascites fluid or into the blood stream of an allogenic host or immunocompromised host.

An immunoprecipitate forms between the antibody and the $p130^{MET}$ which is present in the conditioned medium. The immunoprecipitate is collected, for example on a column such as a Protein-A-Sepharose (Trade Mark) column to which specific anti-Met antibodies have been bound and cross-linked. The $p130^{MET}$ is released from the immunocomplex by treatment with low pH or nigh salt.

A protein according to the invention in which the C-terminal truncated form of the β-chain is the 85 kDa form is prepared according to the invention by a process which comprises:

(i) extracting cells, which express the MET gene, using a detergent;

(ii) contacting the extract with an antibody specific for the extracellular domain of the β-chain of the tyrosine kinase encoded by the MET gene; and (iii) releasing the said protein from the resulting immunocomplex.

The cells which express the MET gene and the culture medium in which they are grown are as described above. The cells are extracted with a detergent, typically a nonionic detergent such as Triton X100 or CHAPS (3-[(3-Cholamidopropyl)dimethylammonio-1-propanesulfonate]). CHAPS is commercially available from Fluka and is used as a 1% solution in HEPS buffer as described in Naldini et al., Molecular and Cellular Biology, Vol. 11, no. 4 (April 1991), pages 1793–1803). Typically the cells are extracted in a buffer. Protease inhibitors may additionally be present such as pepstatin, leupeptin, aprotinin and trypsin inhibitor. The resulting extract is contacted with an antibody specific for the β-chain of the tyrosine kinase encoded by the MET gene and $p140^{MET}$ is released from the resulting immunoprecipitate as described above.

A protein according to the invention can be isolated and purified. It can be provided substantially free of the complete tyrosine kinase encoded by the MET gene and, indeed, substantially free of other components of cells which express the MET gene. The protein can be employed as an antagonist of HGF. The protein maintains the ability to bind to HGF but, being devoid of the tyrosine kinase domain, is unable to transduce the intracellular mitogenic signal. The protein can therefore be used in the treatment of neoplastic diseases, including tumors of the gastrointestinal tract, or the liver, the thyroid and the brain. Actually, a high percentage of these tumors express the HGF receptor and require HGF to grow. It may also be used as a hepatic regeneration-suppressing agent for treatment of liver hyperplasia or adenomatosis.

The protein of the invention may be administered to a patient by any convenient parenteral route. The choice of whether subcutaneous, intravenous or intramuscular administration is adopted; of the dose; and of the frequency of administration depends upon a variety of factors. These factors include the purpose of the administration, the age and weight of the patient being treated and the condition of the patient. A therapeutically effective amount is given. Typically, however, the protein is administered in an amount of from 10 to 1000 μg per dose, more preferably from 50 to 500 μg per dose, for each route of administration.

The protein may be formulated in a pharmaceutical composition. The pharmaceutical composition also comprises a pharmaceutically acceptable carrier or diluent. Any appropriate carrier or diluent may be employed, depending upon the route of administration.

The following Examples illustrate the invention. In the accompanying drawings:

FIG. 1 shows that a truncated form of the Met protein is identified by monoclonal antibodies against the extracellular domain. Panels A and B: GTL-16 cells surface labelled with the $^{125}$I in the presence of lactoperoxidase. Cellular proteins were solubilized with Triton X-100, immunoprecipitated with the different MAbs directed against either the C-terminal peptide (DR-6, lane 1) or the extracellular domain (DO-24, DN-30, DN-31, lanes 2, 3, 4) of the Met protein. Immunoprecipitated proteins were separated by sodium dodecyl sulphate-polyacrylamide gel electrophoresis (SDS-PAGE) under non-reducing conditions (panel A), or after reducing treatment with 2β-mercaptoethanol (panel B). Panel C: the $p140^{MET}$ (lane 1) and the $p190^{MET}$ complexes (lane 2), obtained following immunoprecipitation with DO-24MAbs were excised from the SDS-PAGE, eluted in Laemmli buffer, reduced by 2β-mercaptoethanol and analyzed in SDS-PAGE under reducing conditions. Gels were dried and exposed for autoradiography for 3 days.

FIG. 2 shows two dimensional tryptic peptide maps of the extracellular domains of the β chains isolated from intact or truncated Met receptors. P145$^β$ (panel A), p85$^β$ (panel B) and p75$^β$ (panel C) were separated in SDS-PAGE, following immunoprecipitation with MAbs anti-extracellular domain from either surface radioiodinated GTL-16 cells or supernatant of radioiodinated GTL-16 cells. Proteins were transferred electrophoretically to Immobilon P membrane and subjected to exhaustive tryptic digestion. About 3,000 cpm of each digest were spotted in the right bottom corner corresponding to the anode and subjected to electrophoresis at pH 1.9 and to ascending chromatography in pyridineacetic acid-butanol-water. A major tryptic peptide (arrow) obtained from the α=0 chain of the Met protein is shown for comparison (panel D). The maps were exposed for 2 weeks at −70° C. with intensifying screens. The origin is circled.

FIG. 9 shows the up-regulation of p130$^{MET}$ release from the cell surface by protein kinase C activation. GTL-16 cells were labelled with [$^{35}$S]methionine (100 μCi/ml) overnight, treated for 2 hours with 160 nM TPA dissolved in dimethylsulfoxide (lanes T) or with dimethylsulfoxide alone (lanes C), washed and extracted with non-ionic detergent. Conditioned media (A) and clarified cell extracts (B) were precipitated with MAbs directed against the Met extracellular domain (DO-24). Immunocomplexes, collected on Protein-A-Sepharose, were analyzed in SDS-PAGE under reducing conditions. Gels were fluorographed, dried and exposed for autoradiography for 6 h. Panel C: GTL-16 cells were treated with TPA (lane T) or dimethylsulfoxide (lane C) as described above, labelled with $^{125}$I by lactoperoxidase, washed and extracted with non-ionic detergent. Clarified cell extracts were processed for immunoprecipitation with MAbs DO-24 and immunocomplexes were analyzed as above.

EXAMPLE 1

MATERIALS AND METHODS

Cells

All the lines used are of human origin. GTL-16 cells are a clonal line derived from a poorly differentiated gastric carcinoma (Giordano et al, Mol. Cell. Biol. 8, 3510–3517, 1988). A549 lung adenocarcinoma cells, KB oral carcinoma cells, HT-29 colon carcinoma cells and SK-BR-3 mammary carcinoma cells were purchased from the American Type Culture Collection. Cells were grown in RPMI 1640 medium supplemented with 10% foetal calf serum (Flow Laboratories, Inc. McLean, Va.) in a 5% $CO_2$-water saturated atmosphere.

Antibodies

MAbs against the extracellular domain of the Met protein were obtained following immunization with whole living GTL-16 cells overexpressing the Met protein, according to the procedure of Kohler and Milstein (Nature 256, 495–497, 1975). Immune spleen cells were fused with Ag8.653 myeloma cells and hybrid supernatants were screened in an immunoenzymatic assay (Prat et al, cancer Detection and Prevention, 10, 293–301, 1987) for their differential binding to GTL-16 cells. The hybrid supernatants were screened for their ability to bind selectively to cells overexpressing the Met protein in a solid state immunoenzymatic assay (Prat et al, 1985). For immunoprecipitation tests, cells were labelled for 18 hr with $^{35}$S-methionine, extensively washed and lysed with the non-ionic detergent Triton X100 as previously described (Prat et al, 1985). Samples were analyzed on 8% SDS-PAGE and autoradiographed at −70° C. using Amersham Hyperfilm for 1 day.

Four different MAbs (DL-21, DN-30, DN-31, DO-24) were selected for these studies. The MAbs react with different epitopes of the β-chain, based on reciprocal cross-competition. Since identical results were obtained with different MAbs, for simplicity, we refer to this panel as MAbs anti-extracellular domain. A monoclonal antibody (DR-6) was also raised against a peptide corresponding to nineteen C-terminal amino acids (from $Ser^{1372}$ to $Ser^{1390}$) of the MET sequence (EMBL Data-Bank reference no X54559). Monoclonal antibodies against the extracellular domain of the Epidermal Growth Factor receptor are those described by Honegger et al, EMBO J. 7 (10), 3053–3060, 1988. Unrelated MAbs were used as negative control.

Cell surface iodination, metabolic labelling and immunoprecipitation

Lactoperoxidase-$H_2O_2$-catalyzed cell surface radioiodination was performed as previously described (Giordano et al, 1988). For pulse-chase experiments, cells were pretreated with methionine-free medium for 30 min, pulsed with 400 µCi/ml of [$^{35}$S]-methionine for 15 min, washed twice with complete medium and then chased for different periods of time. Cells were labelled with 100 µCi/ml of either [$^3$H]-glucosamine or [$^{35}$S]-methionine for 18 h. All radioactive isotopes were purchased from Amersham (Amersham Corp., Arlington Heights, Ill). After labelling, cells were extracted with ice cold buffer containing 10 mM Pipes, pH 7.6, 100 mM NaCl, 5 mM $MgCl_2$, 300 mM sucrose, 5 mM EGTA (DIM buffer), 1% Triton X-100 and inhibitors of proteases (pepstatin, 50 µg/ml; leupeptin, 500 µg/ml; aprotinin, 1 µg/ml; 2 mM PMSF, Sigma; soybean trypsin inhibitor, 500 µg/ml, Boehringer). Ultracentrifuged tissue culture supernatants or cell extracts were precleaned on Protein-A-Sepharose and immunoprecipitated with the different antibodies. Immunoprecipitation of molecules exposed at the cell surface was done by incubating intact GTL-16 cells with MAbs before lysis with detergent. Immunocomplexes were collected on Protein-A-Sepharose, previously reacted with affinity purified goat anti-mouse Ig antibodies (GαMlg), washed and eluted in Laemmli (Nature 230, 680–685, 1970) buffer with or without 2β-mercaptoethanol. Tetradecanoyl phorbol acetate (TPA) treatment was performed on GTL-16 cells labelled with [$^{35}$S]methionine for 18 h. Cells were washed with fresh RPMI medium and further incubated with dimethyl sulfoxide containing or not containing (control) 160 nM TPA (Sigma) for 2 h. To analyze the effect of TPA on Met proteins exposed at the cell surface, GTL-16 cells were treated with TPA as described above and then labelled with $^{125}$I by lactoperoxidase. In both cases, cell proteins solubilized with detergent or supernatants were precipitated as described above. Proteins were subjected to SDS-PAGE, fixed, fluorographed when required, dried and exposed to Amersham Hyperfilm for autoradiography.

Immunocomplex kinase assay

Proteins were extracted from GTL-16 cells in DIM buffer, 1% Triton X-100 and precipitated as described above. Immunocomplexes collected on Protein-A-Sepharose-GαMlg, were phosphorylated in 20 µl of the same buffer, in the presence of 2.5 µCi [γ-$^{32}$P]ATP (specific activity, 7,000 Ci/Mm; Amersham) at 30° C. for 5 min. The reaction was stopped by adding 1 ml of ice cold phosphate buffered saline, pH 7.2 containing 5 mM EDTA. Samples were centrifuged and eluted by boiling Laemmli buffer with or without 2β-mercaptoethanol. After SDS-PAGE, gels were dried and exposed to Amersham Hyperfilm for autoradiography with intensifying screens.

Peptide mapping

Met β chains, derived from surface radioiodinated GTL-16 cells, were fractionated by SDS-PAGE and transferred electrophoretically to Immobilon P membranes (Millipore, Towbin et al, PNAS USA 76, 4350–4353, 1979). Membrane fragments containing radioactive β chains were soaked in 0.5% polyvinylpyrrolidone in 100 mM acetic acid at 37° C. for 30 min, washed briefly with water and then with freshly-made 0.05M $NH_4HCO_3$. Tryptic digestion of the immobilized proteins was carried out with 10 µg TPCK-treated trypsin (Worthington) for 16 hr at 37° C. and then for another 2 hr at 37° C. with additional 10 µg of fresh enzyme (Hunter et al, PNAS USA 77, 1311–1315, 1980). Digests were loaded on cellulose thin-layer plates (13255 Cellulose, Kodak), in the corner corresponding to the anode and subjected to electrophoresis at pH 1.9 (2.5% formic acid, 7% glacial acetic acid) for 1200 volt hours. Plates were then subjected to ascending chromatography (n-butanol: pyridine: acetic acid: water, 20:30:6:24 v/v). Peptides were visualized by autoradiography on Amersham Hyperfilm with intensifying screens.

Western blotting

Cells were solubilized in the boiling buffer by Laemmli, with or without the reducing agent 2β-mercaptoethanol. Equal amounts of proteins (300 µg) were loaded into each lane. Samples were analyzed by Western blotting as described by Towbin et al, 1979. Blots were probed with hybridoma supernatant containing DL-21 MAb and then with $^{125}$I-labelled Sheep α-Mlg (Amersham). Autoradiograms were exposed with intensifying screens for 2–3 days. The size of proteins was estimated by using myosin (200 kDa), phosphorylase b (92.5 kDa), bovine serum albumin (69 kDa), egg albumin (43 kDa) and carbonic anhydrase (30 kDa) that had been prelabelled by [$^{14}$C]methylation as markers (Amersham).

Transfection of MET CDFA in NIH 3T3 cells

The expression vector used for these studies was based on plasmid pMT2, containing the major late adenovirus promoter. The expression plasmid was constructed with a 4.3-kb cDNA encompassing the entire MET coding sequence (Giordano et al, 1989, Nature 393 155–156). As this plasmid does not contain any selectable marker, cells were cotransfected with pSV2neo, carrying the neomycin resistance gene. The plasmid was cotransfected into NIH 3T3 cells by the lipofection procedure. Two days after transfection, the neomycin analog G418 was added to the culture medium to select for resistant clones. Stable transfectants expressing Met receptors were identified by assaying for the ability to synthesize Met receptors by Western blot analysis.

RESULTS

A truncated p140$^{MET}$ coexists with p190$^{MET}$ at the cell surface

Figure 1A:
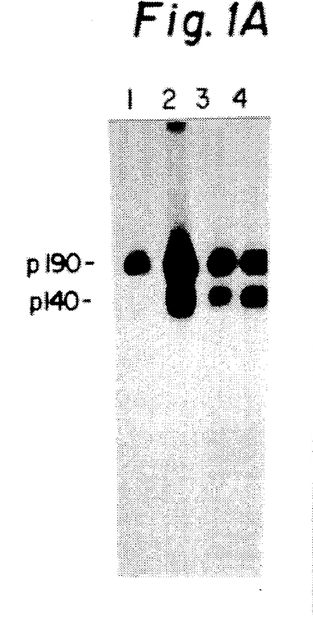
Figure 1B:
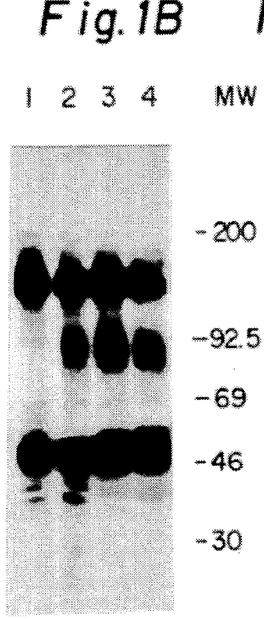
Figure 1C:
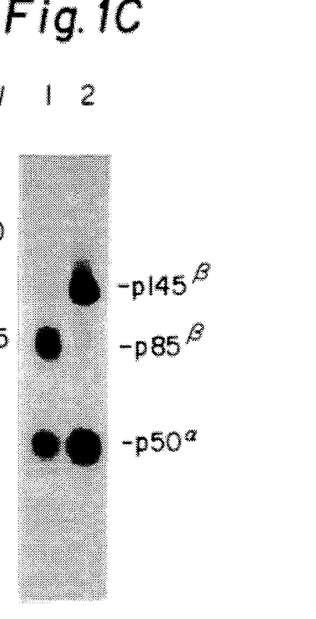

Proteins exposed at the surface of GTL-16 cells were labelled with $^{125}$I by lactoperoxidase. Cells were extracted with 1% Triton and solubilized molecules precipitated with a MAb against the C-terminal peptide of the Met protein, or with MAbs recognizing different epitopes of the extracellular domain. Immunoprecipitates were analyzed in SDS-PAGE under non-reducing or reducing conditions. The antibody against the C-terminal peptide precipitated the p190$^{MET}$ heterodimer (FIG. 1A, lane 1), which was resolved in p50$^\alpha$ and p145$^\beta$ chains under reducing conditions (FIG. 1B, lane 1). MAbs raised against the extracellular domain precipitated with p190$^{MET}$ another molecule migrating at the apparent mol. wt. of 140 kDa (p140$^{MET}$; FIG. 1A, lanes 2, 3, 4). These immunoprecipitates under reducing conditions were resolved in three chains of respectively, 145, 85 and 50 kDa (FIG. 1B, lanes 2, 3, 4) suggesting that p140$^{MET}$ is a heterodimer of p85 and p50. The experiment shown in FIG. 1C, formally proves this interpretation of the heterodimeric structure of p140$^{MET}$. The 140 kDa band excised from panel A, re-run under reducing conditions, originated p85 and p50 (FIG. 1C, lane 1). The latter co-migrated with p50$^\alpha$ dissociated from the p190$^{MT}$ $\alpha\beta$ complex (FIG. 1C, lane 2). The ratio of p190$^{MET}$ to p140$^{MET}$ varied between 1:1 to 2:1. Identical results were obtained when surface iodinated proteins from other cell lines were examined.

Figure 2A:
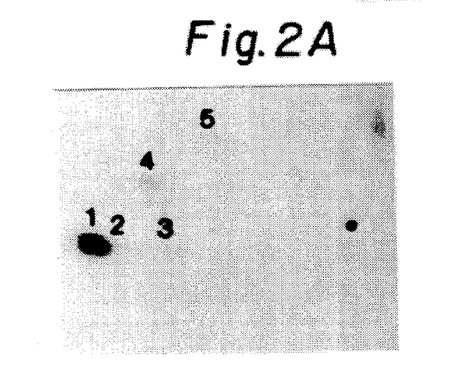
Figure 2B:
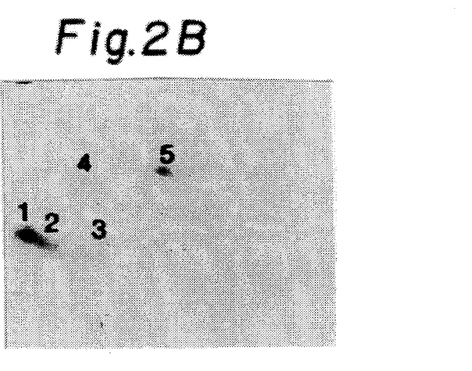
Figure 2C:
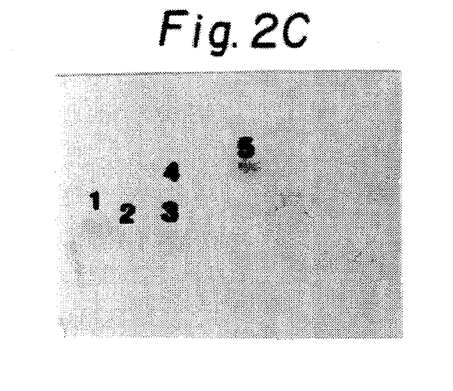
Figure 2D:
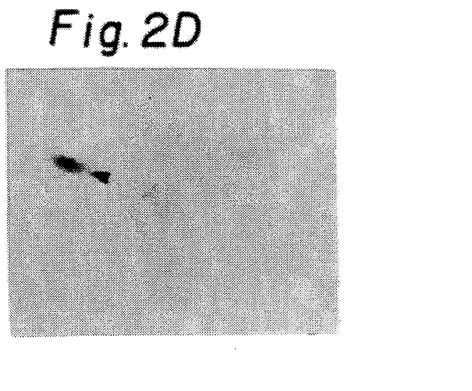

Bidimensional tryptic maps of surface-iodinated p145$^\beta$ and p85$^\beta$ chains show that the extracellular domains of the intact and truncated $\beta$ chains of the Met protein contain identical peptides (FIG. 2A, 2B). In conclusion, p140$^{MET}$ is a heterodimer of p50$^\alpha$ and an 85 kDa $\beta$ chain (p80$^\beta$), deriving from a C-terminal truncation of p145$^\beta$.

The truncated p140$^{MET}$ is not phosphorylated on tyrosine

Figure 3A:
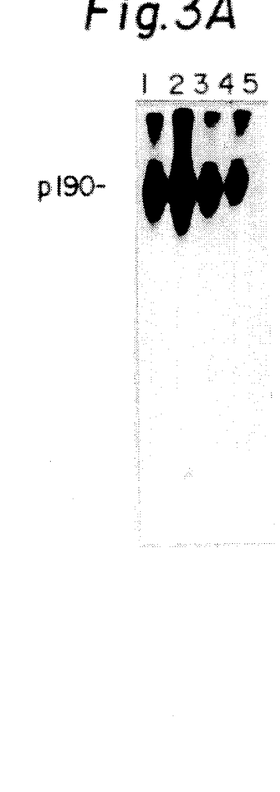
FIG. 3 shows that $p140^{MET}$ is not phosphorylated in vitro. Proteins solubilized from GTL-16 cells in non-ionic detergent were immunoprecipitated with MAbs anti-extracellular domain of the Met protein (DL-21, DO-24, DN-30, DN-31, lanes 1, 2, 3, 4) or with MAbs against an unrelated protein (lane 5). Washed immunocomplexes were phosphorylated in the presence of [γ-$^{32}$P]ATP and labelled proteins were separated by SDS-PAGE under non-reducing conditions (panel A) or reducing conditions (in the presence of 2β-mercaptoathanol, panel B). Gels were dried and exposed for autoradiography for 2 days. Only the intact p190$^{MET}$, or the intact p145$^β$ chain and the Pr170Met precursor are labelled.
Figure 3B:
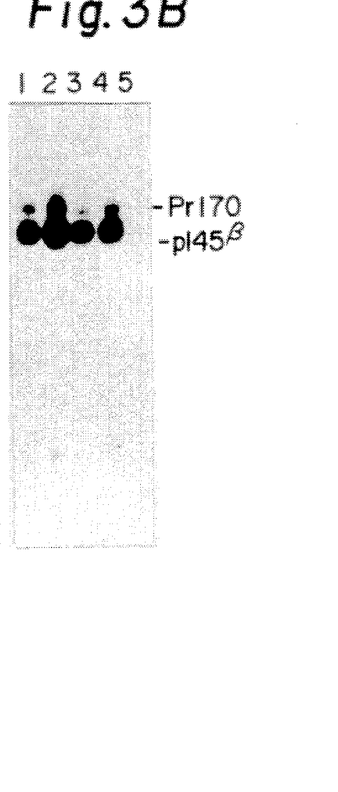

It was previously shown, using antibodies specific for the C-terminal peptide of p190$^{MET}$, that this protein can be phosphorylated in vitro on its S subunit (Giordano et al, 1988). Incubation of immunoprecipitates obtained with the four MAbs directed against Met extracellular domain in the presence of [γ-32P]ATP, results in labelling of p190$^{MET}$ but not of p140$^{MET}$ (FIG. 3A). Under reducing conditions, only p145$^\beta$ was labelled (FIG. 3B). Moreover, p140$^{MET}$ was never decorated by anti-phosphotyrosine antibodies in Western blots of GTL-16 proteins, while p190$^{MET}$ was consistently visualized (Giordano et al, 1988). These data suggest that the truncated form of the Met protein lacks the tyrosine residues that can be phosphorylated in vitro or in vivo.

The truncated p140$^{MET}$ and p130$^{MET}$ originate by processing of p190$^{MET}$

P140$^{MET}$ could either arise from translation of an alternatively spliced mRNA encoding only the extracellular and the transmembrane domains of the Met protein, or it could result from post-translational processing of the intact molecule. Indeed, four different MET transcripts are detected in GTL-16 cells (Giordano et al, Nature 339, 155–156, 1989; Park et al, Cell 45, 895–904, 1986), but none of them lacks the region coding for the cytoplasm domain.

Figure 4:
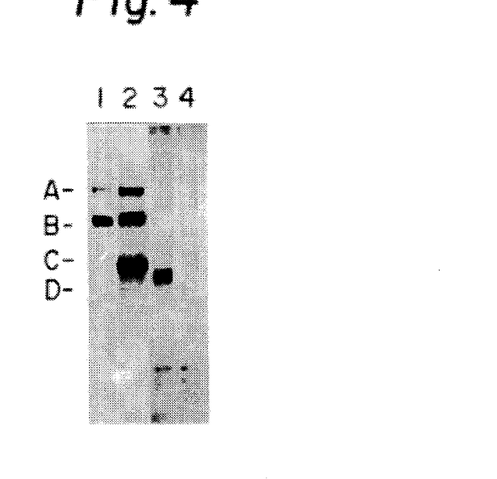
FIG. 4 shows that mouse fibroblasts transfected with the human MET cDNA express intact P190$^{MET}$ as well as truncated forms. Proteins solubilized in boiling Laemmli buffer from NIH 3T3 cells, transfected with the full length MET cDNA derived from the major 9 kb mRNA (lanes 1, 2) or from their conditioned media (lane 3 and 4) were analyzed by Western blot under reducing conditions. Lanes: 1 and 4, MAbs against the C-terminal peptide of the Met protein; 2 and 3, MAb (DO-24) directed against the Met extracellular domain. Specific binding was detected by the enhanced chemiluminescence system (ECLTM, Amersham). Bands A to D have sizes consistent with the 170 kDa Met precursor (A), with the intact p145$^β$ (B), with the truncated p85$^β$ (C) and with the soluble p75$^β$ (D).

To investigate the origin of the C-terminal truncated Met protein, NIH 3T3 cells were cotransfected with the full-length human MET cDNA and pSV2neo. Stable transformants were selected with G418 and analyzed for Met expression. Northern (RNA) blot analysis of positive cells detected a single mRNA of the expected size (approximately 4.3 kb). Cells were solubilized in boiling Laemmli buffer, and proteins were examined under reducing conditions by Western blot. The antibodies against the Met C-terminal peptide detected the 170-kDa Met precursor and the p145$^\beta$ chain (FIG. 4, lane 1). In addition, the antibodies directed against the Met extracellular domain detected a molecule with antigenic properties and molecular weight consistent with those of the truncated p85$^\beta$ (FIG. 4, lane 2). Moreover, in the supernatants of the transfected cells, these antibodies detected a molecule comparable to the soluble p75$^\beta$ (FIG. 4, lane 3). In transfected NIH 3T3 cells, the ratio of the truncated Met $\beta$ chains to the intact one was higher than in human cells. These data show that the Met truncated forms originate from the full-length transcript.

Uneven Cellular distribution of D190$^{MET}$ and p140$^{MET}$

Figure 5:
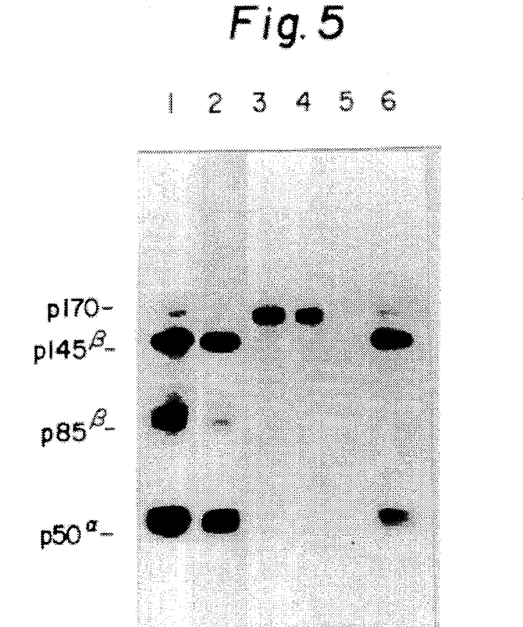
FIG. 5 shows the uneven cellular localization of p190$^{MET}$ and p140$^{MET}$. GTL-16 cells were labelled with [$^3$H]glucosamine for 18 h. Living cells were incubated for 2 h on ice with MAbs before being lysed with detergent (lanes 1, 3, 5). Alternatively cells were lysed first and then incubated with MAbs (lanes 2, 4, 6). In both cases immunocomplexes were recovered with Protein-A-Sepharose and radiolabelled proteins analyzed in SDS-PAGE under reducing conditions. The following antibodies were used: MAbs directed against the extracellular domain (DO-24, lanes 1, 2), or against the C-terminal peptide of the Met protein (DR-6, lanes 5, 6), and MAbs against the extracellular domain of the receptor for EGF (lanes 3, 4). Gels were dried and exposed for autoradiography for 4 days.

To quantitate the relative amounts of p190$^{MET}$ and p140$^{MET}$ in the whole cell and at the cell surface, GTL-16 cells were labelled with [$^3$H]-glucosamine. Using this isotope, the two molecular species should be labelled with similar efficiency, since glycosylation involves only the common extracellular domain. Selective immunoprecipitation of molecules exposed at the cell surface was done (see Methods). The amount of proteins recovered was compared with that immunoprecipitated from whole cell extract. FIG. 5 shows that at the cell surface the ratio of p145$^\beta$ vs p85$^\beta$ was approximately 2:1 (FIG. 5, lane 1). Conversely, in the whole cell extract p85$^\beta$ was not more than ⅒ of p145$^\beta$ (FIG. 5, lane 2). Anti-C-terminus MAbs precipitated p145$^\beta$ only from cell extracts (FIG. 5, lanes 5, 6). It thus can be concluded that the truncated Met form preferentially localizes at the cell surface.

Since the same lysis procedure was used to precipitate Met proteins from the surface or from the whole cell extracts, this experiment further indicates that the potential proteolytic activity induced by detergent does not play a significant role in the generation of p85$^\beta$.

P140$^{MET}$ is not the result of experimentally-induced proteolysis

Proteolytic cleavage of P190$^{MET}$ could be induced by activation of enaogenous protease(s) during cell extraction. As an internal control for post-lytic proteolysis, we used antibodies specific for the extracellular domain to immunoprecipitate the Epiderman Growth Factor receptor. This receptor is expressed in GTL-16 cells (Giordano et al, 1988) and it is known to be susceptible of proteolysis (Basu et al, Nature 311, 477–480, 1984). FIG. 5 shows that under the conditions where the truncated P140$^{MET}$ was observed, only the intact 175 kDa EGF receptor molecule was precipitated, both from the surface and whole cell lysate.

Figure 6:
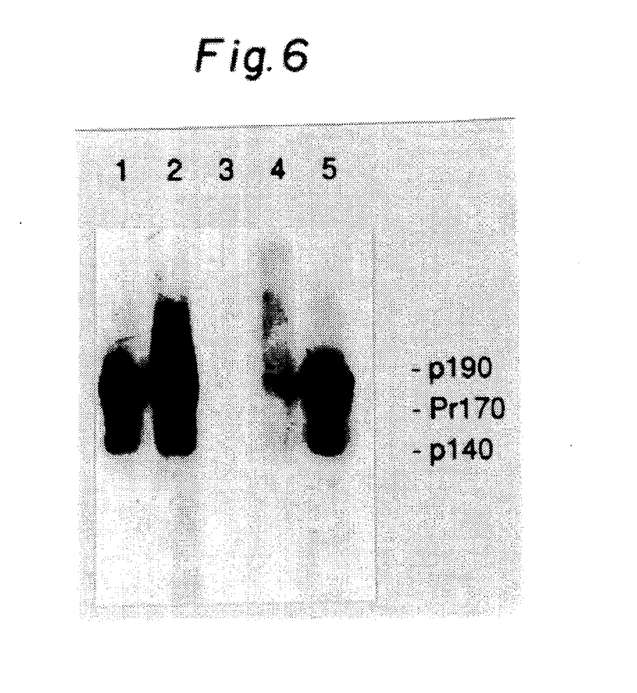
FIG. 6 shows the expression of p140$^{MET}$ in different human cell lines under physiological conditions (Western blot). Cellular proteins were solubilized in boiling Laemmli buffer, separated on SDS-PAGE under non-reducing conditions, transferred to nitrocellulose sheet and decorated sequentially with DL-21MAbs and [$^{125}$I]-Sheep α-mouse Ig. In each lane 300 μg of cellular proteins were loaded; in GTL-16 lane 100 μg were loaded. Cell lines are as follows; lane 1: A549, lung carcinoma, lane 2: GTL-16, gastric carcinoma; lane 3: SK-BR3, mammary carcinoma; lane 4: HT-29, colon carcinoma; lane 5: KB, oral carcinoma.

To further rule out that the truncated form of the Met protein was the result of proteolytic degradation introduced during the extraction or immunoprecipitation procedures, its presence was analyzed directly in Western blots of different human cell lines. In these experiments, living cells were solubilized with boiling Laemmli buffer to block protease activity. Total proteins were separated in SDS-PAGE under non-reducing conditions and decorated with MAbs directed against the extracellular domain. Both p190$^{MET}$ and p140$^{MET}$ forms were observed in four carcinoma cell lines expressing the MET gene (FIG. 6). These data suggest that the truncated form of the Met protein is present in physiological conditions in living cells.

A truncated soluble p130$^{MET}$ is released in the culture medium

Figure 7A:
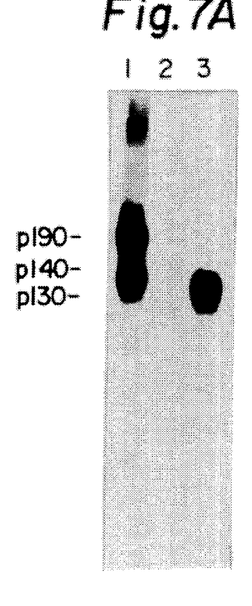
FIG. 7 shows that a soluble truncated form of the Met protein is identified by monoclonal antibodies against the extracellular domain. GTL-16 (panels A, C) or A549 cells (panel B) were labelled with [$^{35}$S]methionine overnight (100 μCi/ml), washed and extracted with non-ionic detergent. Clarified cell extracts (lanes 1) and conditioned media (lanes 2, 3) were precipitated with MAbs directed against the extracellular domain (DO-24, lanes 1, 3) or against the C-terminal peptide (DR-6, lanes 2) of the Met protein. Immunoprecipitated proteins were separated on SDS-PAGE under non-reducing conditions (panels A, B), or after reducing treatment with 2β-mercaptoethanol (panel C). Gels were fluorographed, dried and exposed for autoradiography for 3 days.
Figure 7B:
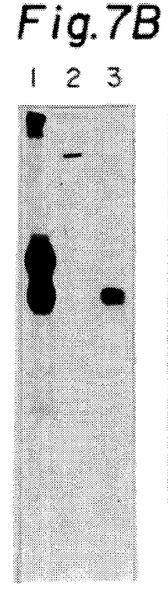
Figure 7C:
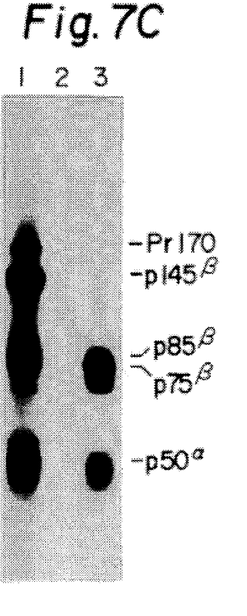

GTL-16 cells were metabolically labelled with $^{35}$S-methionine and the conditioned medium, clarified by ultracentrifugation, was precipitated with MAbs anti-extracellular domain and analyzed in SDS-PAGE. Under non-reducing conditions, a molecule with the apparent mol. wt. of 130 kDa (p130$^{MET}$) was observed (FIG. 7A, lane 3). Upon reduction, this molecule was resolved in two subunits of 50 kDa (p50$^\alpha$) and 75 kDa (p75$^\beta$) respectively (FIG. 7C, lane 3). No proteins were precipitated from the same medium by MAbs against the Met C-terminal peptide (FIG. 7A and 7C, lane 2). Similar results were obtained with a supernatant harvested from the lung carcinoma cell line A549 (FIG. 7B, lane 3).

Tryptic peptide maps were also performed on the p75$^\beta$ chain. As starting material for these experiments were used immunoprecipitates of p130$^{MET}$ released in the culture medium from surface radioiodinated cells. P75$^\beta$ was eluted from SDS-PAGE gels run under reducing conditions. FIG. 3C shows that the labelled tryptic peptides were indistinguishable from those obtained from p145$^\beta$ and p85$^\beta$.

The soluble p130$^{MET}$ is devoid of kinase activity as assessed by the immuno-complex kinase assay in vitro. These data show that the Met form released in the culture medium is an $\alpha\beta$ complex devoid of the cytoplasmic and transmembrane domains of p145$^\beta$ and that the generation of this molecule is not restricted to GTL-16 cells.

P130$^{MET}$ is generated by a proteolytic process

Figure 8:
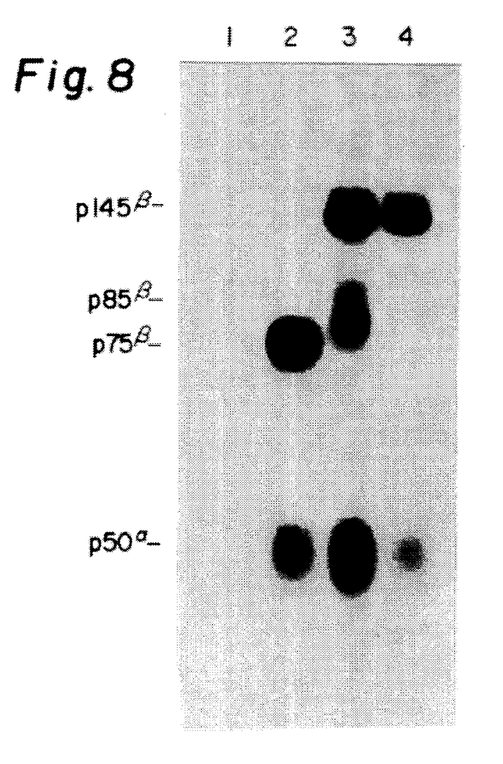
FIG. 8 shows the soluble p130$^{MET}$ is generated by proteolysis of Met proteins exposed at the cell surface. GTL-16 cells were surface labelled with $^{125}$I in the presence of lactoperoxidase. After incubation for 4 h, labelled proteins were isolated either from culture supernatants (lanes 1, 2) or from cell extracts (lanes 3, 4) and immunoprecipitated with MAbs directed against the extracellular domain (DO-24, lanes 2, 3) or against the C-terminal peptide (DR-6, lanes 1, 4) of the Met protein. Immunoprecipitated proteins were separated on SDS-PAGE under reducing conditions. Gels were dried and exposed for autoradiography for 18 hr.

To prove that the soluble p130$^{MET}$ derives from the membrane-bound Met proteins, the following experiment was done. GTL-16 cells adhering to tissue culture plates were surface-labelled with $^{125}$-I by the lactoperoxidase method, and cultured for a further 4 h. Culture medium was harvested and immunoprecipitated with MAbs anti-extracellular domain. The immunoprecipitate, analyzed in SDS-PAGE under reducing conditions, yielded the p75$^\beta$ and the p50$^\alpha$, the expected subunits of soluble p130$^{MET}$ (FIG. 8, lane 2). The corresponding cell extracts treated with the same MAbs yielded p145$^\beta$, p80$^\beta$ and p50$^\alpha$ (FIG. 8, lane 3). MAbs directed against the Met C-terminal peptide were used as control. These antibodies did not precipitate any protein from the culture medium (FIG. 8, lane 1), and precipitated only the intact p145$^\beta$ and p50$^\alpha$ chains from cell extracts (FIG. 8, lane 4). These results demonstrate that the soluble Met protein is released in the culture medium by proteolytic cleavage of the membrane-bound Met proteins.

p130$^{MET}$ release is up-regulated by TPA treatment

Figure 9A:
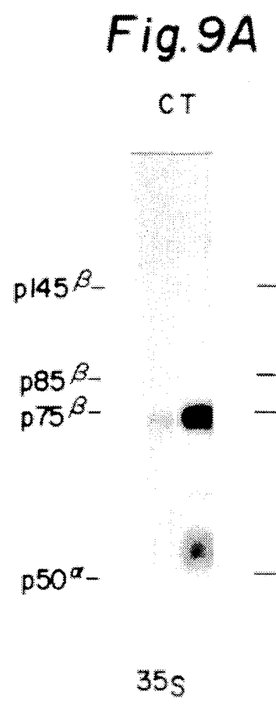
Figure 9B:
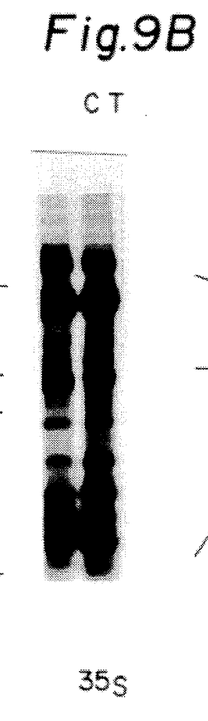
Figure 9C:
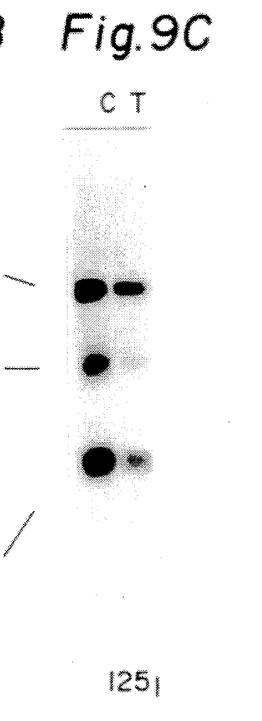

To investigate whether the release of P130$^{MET}$ can be modulated in living cells, protein kinase C was activated by TPA treatment. GTL-16 cells, metabolically labelled with [$^{35}$S]methionine, were stimulated by 160 nM TPA for 2 h. Cell extracts and supernatants were then harvested, ultracentrifuged, and precipitated with MAbs against Met extracellular domain. Immunoprecipitates were analyzed by SDS- PAGE under reducing conditions. Following TPA treatment, the amount of p75$^\beta$ detected in the tissue culture supernatant was significantly increased compared with control levels (FIG. 9A). The amount of total cellular p145$^\beta$ and p85$^\beta$ was apparently unaffected (FIG. 9B). To analyze the effect of TPA on Met proteins exposed at the cell surface, GTL-16 cells were treated with TPA and then labelled with $^{125}$I by lactoperoxidase before immunoprecipitation. When only the surfaced-labelled Met proteins were considered, the amount of p85$^\beta$ was significantly decreased after TPA treatment. p145$^\beta$ was less affected than p85$^\beta$ (FIG. 9C). It is thus concluded that protein kinase C activation up-regulates the release of the extracellular p130$^{MET}$ by stimulating proteolytic processing of the membrane-bound p140$^{MET}$ and p190$^{MET}$ forms.

EXAMPLE 2

MATERIALS AND METHODS

Reagents

[$\gamma$-$^{32}$P]ATP (specific activity: 7000 Ci mmol$^{-1}$) and [$^{125}$I] protein A were obtained from Amersham. $^{125}$I-HGF was prepared as described by Naldini et al. (1991, EMBO J., 10, 2867–2878). Briefly, pure HGF (1 μg) was radio-labelled with carrier free Na$^{125i}$ (2 mCi) and iodogen (Pierce). 200 μl of iodogen at 100 μg/ml in chloroform were dried in a polypropylene vial under nitrogen flow. HGF and $^{125i}$ were then added in 0.25M phosphate buffer pH=7.4. The reaction was allowed to proceed for 15 minutes at 4° C., then the mixture was transferred to another vial and left on ice for 10 minutes. Carrier BSA was added to a final concentration of 0.1% in 0.4M NaCl, 0.1% CHAPS, 20 mM PO$_4$ buffered to PH=7.4 and the labelled ligand was fractionated from the free Na$^{125i}$ by affinity chromatography on a 1 ml heparin-Sepharose column (Pierce) preequilibrated with the same buffer. After extensive washing, the column was eluted with 1.3M NaCl in the same buffer and 0.5 ml fractions were collected. Fractions containing TCA-precipitable radioactivity were pooled, concentrated with a Centrisart (Sartorius) diafiltration apparatus with a membrane cut off of 20 kd and stored at 4° C. The specific activity of the tracer was approximately 8×10$^7$ CPM/μg (5700 Ci/mmole), corresponding to a I/HGF molar ratio of approximately 3/1. Thus, the preparation did not contain a significant amount of unlabelled molecules.

Lentil Lectin Sepharose and Sepharose Protein-A were from Pharmacia. Triton X-100 was from Fluka.

Cells

The cell line used was the GTL-16 cell line as described in Example 1. Cells were cultured in RPMI 1640 medium (Flow) containing 10% of fetal bovine serum (Flow) and maintained at 37° C. in a humidified atmosphere with 5% CO$_2$.

Antibodies

Phosphotyrosine antibodies were raised against p-aminobenzene-phosphonate and affinity-purified as previously described (Comoglio et al., 1984, EMBO J., 3, 483–489). Polyclonal anti-Met serum was raised in rabbits immunized against the synthetic peptide VDTRPASFWETS corresponding to the amino acid sequence at the C-terminal end of the predicted MET gene product. The monoclonal antibodies DN-30, DN-31 and DO-24 against the extracellular domain of the Met protein were obtained in mice following immunization with whole living GTL-16 cells.

The monoclonal antibodies were purified from ascites by ammonium sulfate precipitation and affinity chromatography on Protein A-Sepharose 4B (Pharmacia, Uppsala, Sweden). The purified DO-24MAb was labelled with $^{125}$I by the chloramine T procedure at a specific activity of 2–4 mCi/mg protein.

Partial purification of p130$^{MET}$

Serum-free conditioned medium was harvested from GTL-16 confluent cultures, ultracentrifuged at 50,000× g, concentrated on Amicon filters (100K) 10 fold (stock solution). Purification was performed by affinity chromatography on a Lentil Lectin Sepharose column. After 2 hr at 4° C. the column was washed several times with RPMI medium and glycoproteins eluted with RPMI containing 0.2M α-methyl-D-Mannoside (Fluka). After an overnight dialysis against RPMI, part of the affinity chromatography purified material was depleted of p130$^{MET}$ by exhaustive adsorption on MAb DN-31 insolubilized on Sepharose-Protein A. This material was used as negative control. The solution of partially purified p130$^{MET}$ was standardized at a protein concentration containing 0.4 O.D. units (280 nm). The glycoprotein was stored at −20° C.

Double Determinant Immuno Assay (DDIA)

96-well ELISA plates (Titertek Immuno Assay-Plate, Flow Laboratories, Netherlands) coated with the DN-30 MAb and saturated with BSA were incubated overnight at 4° C. with different concentrations of partially purified p130$^{MET}$ and radiolabelled HGF. In the DDIA developed to evaluate the amount of p130$^{MET}$, two MAbs directed against different epitopes of the extracellular domain of Met proteins were used. Purified DN-30MAbs was adsorbed on 96-well ELISA plates, plates were then saturated, and different concentrations of crude supernatant harvested from GTL-16 cell cultures were added. Binding was revealed by radiolabelled DO-24MAb used as tracer. The plates were then extensively washed and the bound radioactivity eluted with 1% boiling SDS and counted in a gamma-counter (Autogamma, Packard).

Immunoprecipitation and in vitro autophosphorylation assay

GTL-16 cells were washed twice with ice-cold PBS and lysed in DIM buffer (10 mM Pipes, pH 6.8, 100 mM NaCl, 5 mM MgCl$_2$, 300 mM sucrose, 5 mM EGTA) plus 1% Triton x-100 and a mixture of protease inhibitors. The cell lysates were centrifuged at 10,000 rpm at 4° C. for 30 min and incubated with anti-MET serum coupled to Sepharose-protein A. Bound proteins were washed several times in DIM buffer and incubated for 5 min at room temperature with 60 μl of different dilution of Lentil Lectin eluate of GTL-16 supernatant depleted or not of p130$^{MET}$. The kinase reaction was performed on ice for 2 min. 10 μCi of [γ-$^{32}$P] ATP per sample were diluted with 100 μM final concentration of unlabelled ATP. The kinase reaction was stopped with 1 ml of Tris-buffered saline with 10 mM EDTA and 100 μM Na$_3$VO$_4$. After a brief centrifugation proteins were eluted in boiling Laemmli buffer and subjected to 8% SDS-PAGE followed by autoradiography for 12 h at −80° C. with intensifying screens. The relative amount of phosphate incorporated in p145$^{MET}$ β-subunit was estimated by measuring the optical density of the corresponding autoradiography band with a laser densitometer (Pharmacia LKB 2202 Ultroscan).

Western blotting

Cellular monolayer of GTL-16 cells were washed twice with ice-cold phosphate buffered saline and cells solubilized in boiling Laemmli buffer (Laemmli, U.K., 1970, Nature 230, 680–685). Samples were adjusted to a protein concentration of 300 μg/well, run in 8% SDS-PAGE and transferred onto nitrocellulose sheets. Blots were probed with 10 μg ml$^{-1}$ of purified P-Tyr antibodies followed by [$^{125}$I]-labelled protein A as described in detail elsewhere (Di Renzo et al., 1986, Eur. J. Biochem., 158, 383–391). Filters were subjected to autoradiography for 24 hr at −70° C. using intensifying screens. The relative amount of phospho-tyrosine incorporated in p145$^{MET}$ β-subunit was estimated by measuring the optical density of the corresponding autoradiography band with a laser densitometer.

Results

HGF binds to p130$^{MET}$

Figure 10:
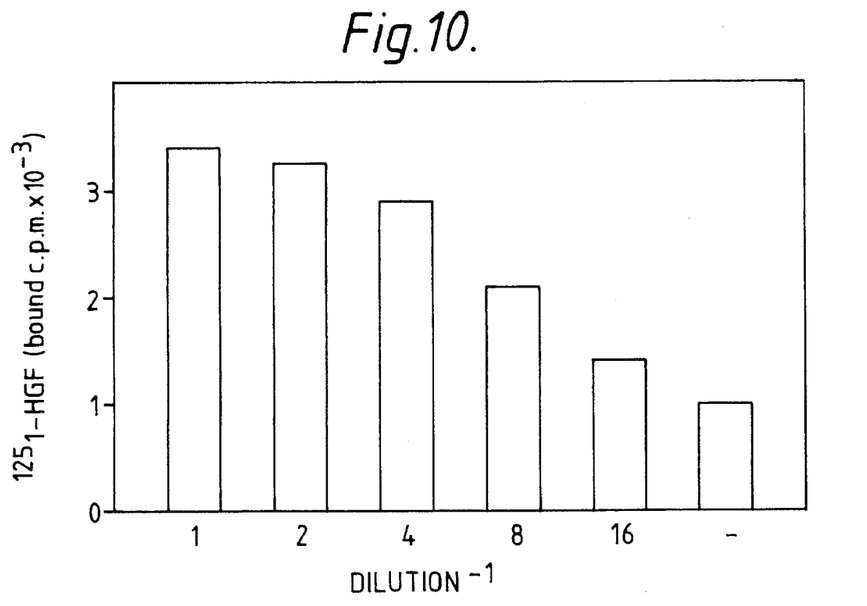
FIG. 10 shows the binding of $^{125}$I-HGF by soluble p130$^{MET}$MAb DN-30 directed against the extracellular domain of Met protein was coated on PVC microtiter wells and used as catcher for different concentrations of p130$^{MET}$ or conditioned medium deprived of p130$^{MET}$(−). $^{125}$I-HGF was then added as described in Example 2 under Materials and Methods. Plates were incubated overnight at 4° C., washed 3 times and bound radioactivity was eluted with 1% SDS and measured in a γ-counter.

FIG. 10 shows that increasing amounts of soluble truncated p130$^{MET}$, insolubilized onto microtiter wells coated with specific antibodies, binds radiolabelled HGF. The binding is saturable and dose-dependent.

Figure 11:
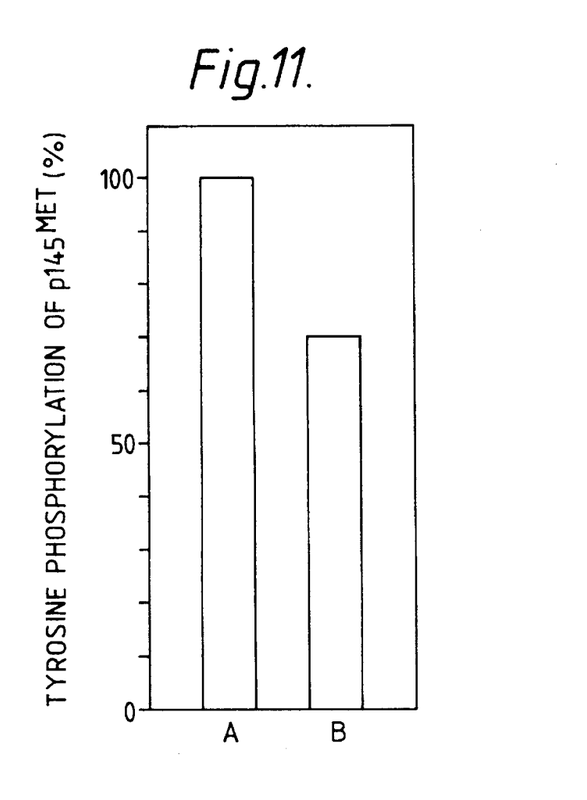
FIG. 11 shows the inhibition of the in vivo tyrosine phosphorylation of the HGF receptor (p145$^β$ subunit) by soluble p130$^{MET}$.GTL-16 cells were incubated with p130$^{MET}$ partially purified by affinity chromatography on Lentil Lectin, as described in Example 2 under Materials and Methods. The relative amount of phosphotyrosine present in P145$^β$ was estimated by measuring the optical density of the corresponding band observed in radiograms of Western blots probed with P-Tyr antibodies. The values shown are from a representative experiment. A: Cells incubated with conditioned medium depleted of p130$^{MET}$, B: Cells incubated with Lentil Lectin purified p130$^{MET}$.

Inhibition of in vivo tyrosine phosphorylation of the MET/HGF receptor by p130$^{MET}$ GTL-16 cells express a high amount of the HGF receptor whose β subunit (p145) is constitutively phosphorylated on tyrosine in vivo. This can be assessed by Western blot of total cellular proteins solubilized with ionic detergent, analyzed in SDS-PAGE and probed with P-Tyr antibodies (FIG. 11,A). Treatment of these cells, for 10 min, with lentil-lectin purified p130$^{MET}$ induced a 30% decrease in tyrosine phosphorylation of the HGF/SF receptor (FIG. 11,B).

Figure 12:
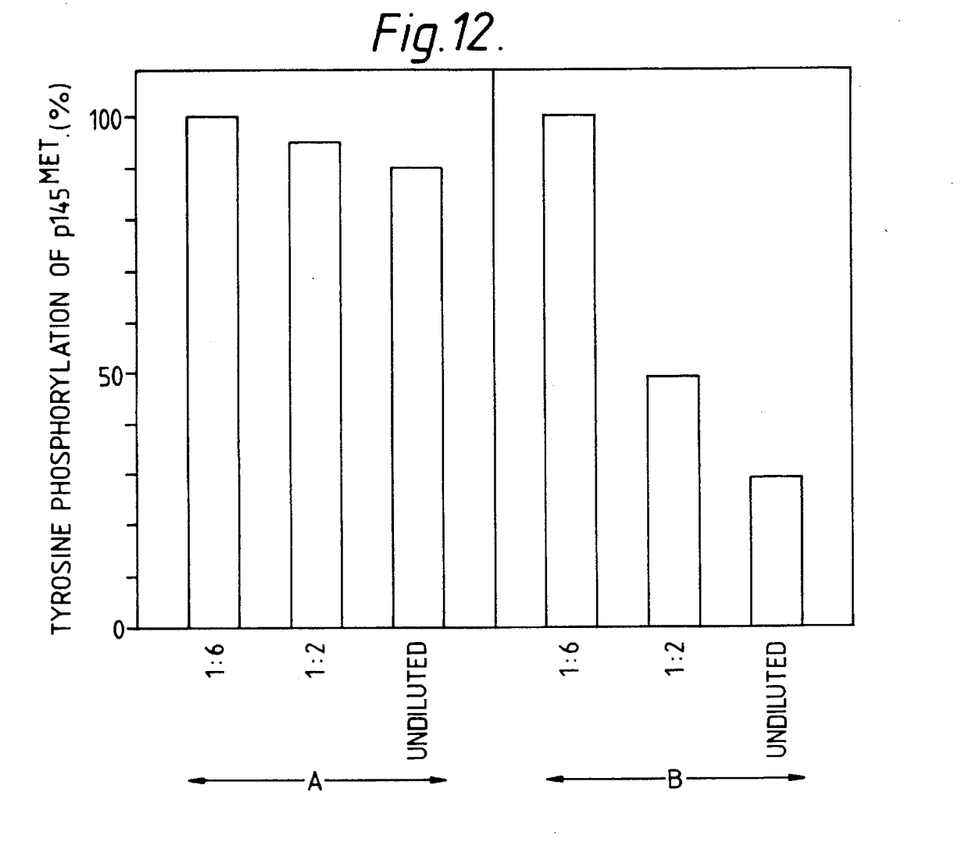
FIG. 12 shows the inhibition of the in vitro tyrosine kinase activity of the Met/HGF receptor (p145$^β$ subunit) by soluble p130$^{MET}$. The receptor was precipitated with polyclonal anti-Met serum and incubated for 5 min at room temperature with 60 μl of different dilutions of conditioned medium depleted of p130$^{MET}$ (A) or partially purified p130$^{MET}$ (B). The kinase reaction was performed on ice for 2 min in the presence of 100 μM [γ-$^{32}$P]ATP and 5 mM MgCl$_2$. After SDS-PAGE and autoradiography, the kinase activity was quantified by measuring the optical density of the $^{32}$P-labelled band with a laser densitometer. The values shown are from a representative experiment.

Inhibition of tyrosine kinase activity in vitro of the Met/HGF receptor by p130$^{MET}$ The HGF receptor was immunoprecipitated from GTL-16 cells with an antiserum directed against a synthetic peptide derived from the C-terminal sequence of the protein. The p130$^{MET}$ incubated with the immune complexes prior to the kinase assay, inhibited in a dose-dependent manner the autophosphorylation of the intact receptor β subunit (p145$^{MET}$; FIG. 12,B). Only a slight inhibitory effect was measured with the same concentrations of lentil-lectin eluates depleted of p130$^{MET}$ (FIG. 12,A).

Figure 13:
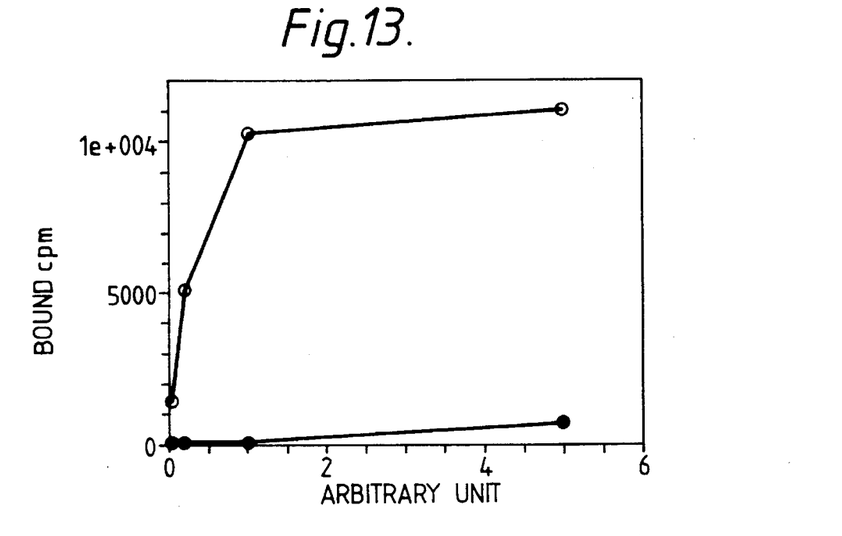
FIG. 13 illustrates the radioimmunometric detection of soluble p130Met released from GTL-16 cells in the tissue culture medium. Open circles : GTL-16 supernatant; closed circles: RPMI medium (negative control).

Quantification of soluble p130$^{MET}$ by DDIA p130$^{MET}$ can be quantitatively evaluated by a solid-phase double determinant immunoassay using a tandem of MAbs recognizing different epitopes. FIG. 13 shows a typical binding curve obtained with p130$^{MET}$ released from GTL-16 cells in the tissue culture medium. The binding is saturable, dose-dependent and specific.

We claim:

1. An isolated and purified protein comprising two disulfide linked chains of 50 kDa and either 75 or 85 kDa, wherein the 50 kDa chain is an α-chain of a tyrosine kinase encoded by a MET protooncogene and the 75 or 85 kDa chain is a C-terminal truncated form of a β-chain of said tyrosine kinase.

2. A composition, comprising a protein according to claim 1 in combination with a carrier or diluent.

* * * * *